United States Patent
Borchardt et al.

(10) Patent No.: US 10,682,452 B2
(45) Date of Patent: Jun. 16, 2020

(54) APPARATUS FOR EXCHANGING MATERIAL BETWEEN BLOOD AND A GAS/GAS MIXTURE

(71) Applicant: enmodes GmbH, Aachen (DE)

(72) Inventors: Ralf Borchardt, Aachen (DE); Tim Kaufmann, Aachen (DE)

(73) Assignee: ENMODES GMBH, Aachen (DE)

(*) Notice: Subject to any disclaimer, the term of this patent is extended or adjusted under 35 U.S.C. 154(b) by 299 days.

(21) Appl. No.: 15/527,056

(22) PCT Filed: Jan. 7, 2016

(86) PCT No.: PCT/EP2016/000008
§ 371 (c)(1),
(2) Date: May 31, 2017

(87) PCT Pub. No.: WO2016/110446
PCT Pub. Date: Jul. 14, 2016

(65) Prior Publication Data
US 2017/0361000 A1    Dec. 21, 2017

(30) Foreign Application Priority Data
Jan. 7, 2015   (DE) .................. 10 2015 000 021

(51) Int. Cl.
*A61M 1/16*    (2006.01)
*A61M 1/10*    (2006.01)
*A61M 1/12*    (2006.01)

(52) U.S. Cl.
CPC .......... *A61M 1/1698* (2013.01); *A61M 1/106* (2013.01); *A61M 1/12* (2013.01); *A61M 2205/04* (2013.01); *A61M 2205/3341* (2013.01); *A61M 2205/8275* (2013.01); *A61M 2205/8281* (2013.01); *A61M 2206/22* (2013.01)

(58) Field of Classification Search
CPC ................ A61M 1/1698; A61M 1/106; A61M 2205/8275; A61M 1/1037; A61M 1/12; A61M 2206/22; A61M 2205/8281; A61M 2205/3341; A61M 2205/04
See application file for complete search history.

(56) References Cited

U.S. PATENT DOCUMENTS

| 8,398,858 B2 | 3/2013 | Kashefi-Khorasani | |
| 8,409,502 B2* | 4/2013 | Mortensen | A61M 1/16 422/45 |

(Continued)

*Primary Examiner* — Leslie R Deak
(74) *Attorney, Agent, or Firm* — Andrew Wilford

(57) ABSTRACT

The invention relates to an apparatus for exchanging material between blood and a gas/gas mixture, comprising a chamber (1) through which blood can flow and in which a plurality of material-permeable fiber tubes is provided, the gas/gas mixture being flowable through the fiber tubes, blood being flowable around the fiber tubes. At least one deformable element (9) is provided in the chamber (1) in addition to the fiber tubes, through which the gas/gas mixture can flow, this deformable element being deformable and restorable, in particular compressible out of a relaxed shape and restorable to a relaxed shape by pressure fluctuations acting on the at least one element (9) externally, in particular pressure fluctuations transmitted by the blood in the chamber (1).

13 Claims, 1 Drawing Sheet

(56) References Cited

U.S. PATENT DOCUMENTS

| | | |
|---|---|---|
| 2002/0143397 A1* | 10/2002 | von Segesser ............ A61F 2/04 623/9 |
| 2004/0052681 A1 | 3/2004 | Mortensen et al. |
| 2010/0106072 A1 | 4/2010 | Kashefi-Khorasani et al. |
| 2014/0061116 A1 | 3/2014 | Schmitz-Rode et al. |
| 2014/0143397 A1 | 5/2014 | Gutt et al. |

* cited by examiner

APPARATUS FOR EXCHANGING MATERIAL BETWEEN BLOOD AND A GAS/GAS MIXTURE

CROSS REFERENCE TO RELATED APPLICATIONS

This application is the US-national stage of PCT application PCT/EP2016/000008 filed 7 Jan. 2016 and claiming the priority of German patent application 102015000021.7 itself filed 7 Jan. 2015.

FIELD OF THE INVENTION

The invention relates to an apparatus for exchanging material between blood and a gas/gas mixture, comprising a chamber through which blood can flow, and in which a plurality of material-permeable fiber tubes is provided, wherein the gas/gas mixture can flow through the fiber tubes, and blood can flow around the fiber tubes.

BACKGROUND OF THE INVENTION

An apparatus of this type is known from the prior art and is frequently called an oxygenator and is used to lower the $CO_2$ partial pressure and to raise the $O_2$ partial pressure by material exchange, particularly a gas exchange via the permeable walls of the fiber tubes. For that purpose, a gas or gas mixture is passed through the fiber tubes such that the $CO_2$ partial pressure is lower than in the blood and the $O_2$ partial pressure is higher, resulting in a compensation of the partial pressures through a material exchange due to diffusion of the gas molecules, and thus in oxygen enrichment and $CO_2$ depletion in the blood.

Such an oxygenator or apparatus of the this type can be used as an artificial lung, and according to the previous prior art such an apparatus is essentially used outside the body.

A problem with the use of such an apparatus occurs particularly when it is provided to completely take over the function of the lung, for example in patients waiting for a lung transplant. This is a problem insofar as, due to the flexibility of the pulmonary vessels and particularly the pulmonary artery, a so-called windkessel effect, i.e. an elastic flexibility of the vessels in case of blood fluctuations due to the heartbeat that is provided by these organs or organ regions, is omitted, and since the heart must pump against increased resistance, when a rigid apparatus for material exchange is used, it is medically questionable.

Against this backdrop an apparatus has already been developed, in which the outer housing has a flexible wall that is flexible with regard to the pulsating blood pressure insofar as the housing volume reacts to the blood pressure and increases with elevated blood pressure, and the outer dimensions of the entire apparatus increase in size. The apparatus of the above-described type are large by comparison and not very suitable for a preferred use inside the body.

OBJECT OF THE INVENTION

The object pf the invention is therefore to provide and improve an apparatus of the above-described type that, compared to the prior art, is more compact, provides steady blood flow, can be used outside the body and preferably also inside the body, and with which the right ventricle of the heart can preferably be used as pump for delivering blood through the apparatus, particularly without the heart being stressed beyond a normal level.

SUMMARY OF THE INVENTION

According to the invention, this problem is solved in that in the above-described chamber, in addition to the fiber tubes, at least one deformable element is provided through which the gas/gas mixture can flow or flows, when in use, this deformable element being deformable and restorable, in particular compressible out of a relaxed shape and restorable to the relaxed shape by pressure fluctuations acting on the at least one element externally, in particular pressure fluctuations transmitted by the blood in the chamber.

Unlike the natural windkessel function of the blood vessels, whereby the blood pressure acts on the vascular walls from the inside and expands them in case of pressure increase, the blood pressure in the invention acts externally on the at least one deformable element because it is provided together with the blood in the chamber and surrounded by blood. In case of increasing blood pressure (for example during the systole at natural cardiac activity or caused by a separate pulsatile blood pump), the at least one deformable element is thus compressed, particularly from a relaxed shape, and in case of decreasing blood pressure (for example during the diastole at natural cardiac activity or caused by a separate pulsatile blood pump), the at least one element expands, i.e. is preferably restored to the previous, particularly relaxed shape.

A first essential advantage of such an apparatus is the fact that pressure fluctuations in the blood caused by the heartbeat are not accompanied by an outwardly transmitted volume increase of the entire apparatus, but instead, the pressure fluctuations caused by the heartbeat are internally absorbed in the chamber by the at least one deformable element integrated in the chamber, and in a preferred embodiment, the deformable element can be compressed, i.e. the volume decreases under increasing blood pressure, and can be restored to a relaxed full-volume shape when the blood pressure decreases. According to the invention, the relaxation is caused solely by internal return forces, when the blood pressure decreases, and so such an element must be called passive because it does not contain and require artificial actuator technology in order to induce a heartbeat-synchronous deformation.

The invention can preferably provide that the only function of the at least one deformable element in the apparatus is that of providing the windkessel effect.

According to the invention, at least one such deformable element is provided, and according to a preferred embodiment, an apparatus according to the invention can have a plurality of such deformable elements inside the chamber.

In its simplest design, such a deformable element can be, for example, an elastically deformable element made of an elastic solid material, such as an elastomeric plastic that reacts reversibly after compression due to forces acting from outside. For example, it can be a vulcanized material made of natural or silicone rubber.

For such a deformable element, particularly an elastically deformable plastic is used whose glass transition point lies below the operating temperature of the element in the apparatus according to the invention. In case of use inside the body, this operating temperature is, for example the body temperature of approximately 37° C., and in case of use outside the body, it is the ambient temperature near the body, particularly in the range from 15° C. to 30° C. Preferably, an elastic material can be used that has a tensile modulus smaller than 0.05 kN/mm².

By contrast, in a different preferred embodiment, the at least one deformable element is a hollow body. Such a hollow body can have outer walls made from a deformable material according to the above-described details, particularly from the above-described elastic material, particularly plastic, preferably with the above-mentioned tensile modulus smaller than 0.05 kN/mm².

Such a hollow body that, in a particularly preferred embodiment can be a fibrous or tubular hollow body, thus particularly a longitudinally elongated hollow body, is preferably filled with a fluid, preferably a gas that does not pass through the hollow body. A filling with a liquid can also be provided. The cross-section of such a fibrous or tubular hollow body perpendicular to the longitudinal extension direction is basically arbitrary but preferably circular.

Such a preferably gaseous fluid forms a compressible mass in connection with the deformability of the walls of such a hollow body, thus particularly with the elasticity of a hollow body whose walls are made of an elastic material, particularly plastic.

According to the invention, elastic materials are preferably materials that are suitable to yield under the impact of regular blood pressure (up to a maximum of 200 mm Hg) such that a function similar to the natural windkessel function is achieved, particularly a volume variability between systole and diastole of 20 to 80 ml.

When using fibrous/tubular hollow bodies, the invention can in a preferred embodiment provide that a multiplicity of fibrous/tubular, permeable or preferably impermeable hollow bodies are provided in the chamber, and that these elongated hollow bodies extend parallel to the material-permeable fiber tubes through which gas is exchanged and are surrounded by them. These fibrous/tubular hollow bodies can preferably be uniformly distributed in the entire volume of the chamber.

For example, the fibrous or also tubular hollow bodies that represent a volume compressible under blood pressure influence can be surrounded by the material-permeable fiber tubes while making contact, i.e. adjacent permeable fiber tubes bear against the fibrous/tubular compressible hollow bodies, at least when they are relaxed.

The deformable, preferably fibrous hollow bodies can for example be formed with walls from elastic silicon and thus represent silicon fibers, particularly with the above-described tensile modulus.

Particularly with an arrangement of a multiplicity of deformable fibrous hollow bodies that are between, preferably parallel to the gas-permeable fiber tubes, it is possible that, in addition to the pure volume change between systole and diastole, the flow resistance for the blood in the chamber is reduced during the systole because, due to the compression of the hollow bodies in the systole, the open free flow area between the hollow bodies and fiber tubes is increased.

According to the invention, due to the at least one deformable hollow body, particularly the multiplicity of fibrous or tubular deformable hollow bodies, no flow of preferably gaseous fluid takes place, but that, at best, such a deformable hollow body holds a fluid bubble, preferably a gas bubble, and so fluid, preferably gas, can only flow in and out of the hollow body through preferably only one single outlet of a respective hollow body.

However, it is also possible in one embodiment that a deformable hollow body within the chamber defines a fluid volume, particularly a gas volume or fluid volume that is enclosed on all sides, i.e. it is closed in all directions and has no fluidic connection to an area outside of the chamber.

A preferred embodiment can provide that the at least one deformable hollow body, particularly a multiplicity of fibrous or tubular deformable hollow bodies, similar to the material- and gas-permeable fiber tubes, open(s) into a gas inlet or a gas outlet to which a gas/gas mixture participating in the material exchange is applied or at least can be applied. Preferably, the fibrous hollow bodies as well as the fiber tubes for the gas exchange extend between a gas inlet and a gas outlet, and these hollow bodies according to the invention are preferably closed toward the side of the gas inlet and are open in the direction of the gas outlet, i.e. they open into this gas outlet.

Particularly in case of a continuous gas flow that is provided for the purpose of material exchange in such an apparatus, static pressure that influences the deformability is applied to the fibrous hollow bodies or the at least one deformable hollow body. For example, the static pressure can be influenced at or in a respective hollow body by varying flow velocity.

In general, the invention can provide that a static fluid pressure, preferably gas pressure, is exclusively applied to the interior of the at least one hollow body or the provided fibrous or tubular hollow bodies for providing the windkessel effect, and this pressure can, if necessary, be changed to a different static pressure for the purpose of change. Due to the blood pressure acting from outside, the pressure in the hollow bodies thus varies by the inner static pressure that is present in the absence of blood pressure, particularly, for example before the apparatus is used as oxygenator and filled with blood. The relaxed shape hereby particularly refers to the shape that is present with the at least one hollow body under the influence of the diastolic blood pressure, particularly under the influence of a continuously static pressure of gas predominant inside the hollow bodies.

In such an embodiment that the fibrous or tubular hollow bodies can be made of a gas-permeable material, and so gas can basically also be exchanged through these hollow bodies, even though a gas exchange does not take place due to a gas flow within these hollow bodies. Instead, the hollow bodies are pulsatingly compressed and relaxed to effect a gas exchange. In this embodiment, the hollow bodies do not exclusively provide the windkessel function as described above, but also participate in the gas exchange; however, they continue to be passive, i.e. only the natural blood pressure is periodically applied externally. An inner periodic pressure application still does not take place in this case.

Another embodiment can also provide that the at least one deformable hollow body, particularly a multiplicity of fibrous or tubular deformable hollow bodies, open(s) into a space separate from the chamber that can be filled with gaseous or liquid fluid. For example, a gas or liquid is used in the space that does not participate in the material exchange.

In this embodiment, the deformable hollow bodies essentially only used to provide a windkessel effect can be not permeable with regard to material exchange and ensure that there is no possibility that the gas or gas mixture used in the hollow bodies or the liquid itself participates in the material exchange.

If a gas or gas mixture is applied to the above-described separate space that corresponds to the gas or gas mixture used for the material exchange, it is possible to basically also use a deformable hollow body that has a material permeability for $O_2$ and $CO_2$.

The design with a multiplicity of deformable hollow bodies opening into a separate space ensures that the volume available for compression under the fluctuating blood pressure is greater than the volume encompassed by the hollow bodies themselves, i.e. by the volume quantity formed by the separate space.

In a structurally preferred embodiment, according to the invention the above-described is provided relative to the axial flow direction of the gas in the chamber due to the gas-permeable fiber tubes, upstream of the gas outlet. For that purpose, the material- or gas-permeable fiber tubes can open into the gas outlet that, for example extends annularly or as a disk around the central axis, while the fibrous or tubular hollow bodies that provide the windkessel effect extend through the gas outlet, preferably parallel to the axis of the chamber, and only subsequently open into the space provided axially downstream.

A development according to the invention can furthermore also provide that the fluid pressure, preferably the gas pressure, can be adjusted variably, particularly variably statically in the separate space, for example by an external connection, with which the internal pressure in the space and thus also in the hollow bodies can be changed. It is thus possible to change the resistance of the deformable hollow bodies, particularly the multiplicity of deformable fibrous hollow bodies to the blood pressure and the force thus applied to the hollow bodies.

In a development, the invention can also provide that not only one single fluid-fillable separate space is provided for the hollow bodies to open into, but that, for example, at least two separate spaces are provided, and a first number of fibrous/tubular deformable hollow bodies open into the first separate space, and a second number of other fibrous deformable hollow bodies open into the second space.

This can apply if only one single deformable hollow body is associated with the corresponding space.

For example, it is possible to apply different pressures to these two groups of numbers of deformable hollow bodies and thus adjust the change of shape of the hollow bodes more specifically to individually required needs.

From a structural point of view, it is advantageous that the at least one separate space is provided on one of the two axial ends of the apparatus.

Axial ends of the apparatus refer to those ends that are spaced apart in the direction of the longitudinal extension direction of the permeable fiber tubes and/or the fibrous/tubular hollow bodies. The apparatus can for example have a circular or polygonal cross-section perpendicular to this axial extension direction.

The at least one mentioned separate space can be provided particularly at the axial end opposite the end where both the blood inlet and blood outlet are.

For example, both in the above-described embodiment as well as all other conceivable embodiments of the apparatus according to the invention, the design can be such that a blood inlet and a blood outlet are provided on one of the two axial ends of an apparatus according to the invention. For example, the blood inlet can open into an annular circumferential compartment that surrounds the chamber, and so it is thus possible that the blood can flow from this circumferential area radially relative to the central axis of the chamber into the chamber, and a passage is further provided in the chamber that opens into the blood outlet of the apparatus and preferably coaxial to the central axis of the apparatus and surrounded by the material-permeable fiber tubes and a plurality of fibrous/tubular hollow bodies.

Near the other end opposite the blood inlet and the blood outlet, this passage preferably has at least one opening through which blood can pass from the interior of the chamber into the passage. With this arrangement, it is possible that the blood flows in the apparatus such that it flows from radially outside in the radially inward direction, and that it simultaneously flows from the end at which it flows into the chamber, to the opposite end, and that it subsequently flows within the chamber back to the outlet at the other end.

In this design, the blood can basically also flow in reverse direction, i.e. only blood inlet and blood outlet are interchanged, particularly only functionally but not with regard to design.

In axial extension direction of the apparatus, gas inlet and gas outlet can be constructively realized opposite one another on the two axial ends, wherein the gas flows in the reverse or the same direction as the blood.

BRIEF DESCRIPTION OF THE DRAWING

Preferred embodiments of the invention shall be described in more detail using the drawings described below and in which.

SPECIFIC DESCRIPTION OF THE INVENTION

Figure 1:
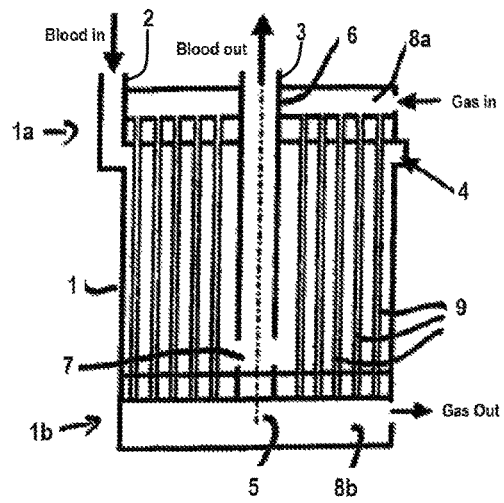
FIG. 1 is a schematic side view of the material-exchange apparatus of the invention.

FIG. 1 shows an embodiment that has a longitudinal extension direction with reference to FIG. 1 from top to bottom, i.e. in the paper plane, whereas perpendicular to the paper plane, the cross-section shape of the apparatus is, for example round. Any other cross-section shape is also possible.

The apparatus comprises a housing that defines a chamber 1 into which blood can flow from a blood inlet 2 to a blood outlet 3. The blood inlet is designed such that blood can flow axially into the inlet; however, due to an annular compartment 4 that surrounds the formed chamber 1 at one axial end, it is diverted to the outer periphery of the chamber 1 at this axial end in order to subsequently flow from this annular compartment 4 radially inward into the chamber 1.

In terms of the longitudinal extension direction and the central axis 5 of the chamber 1, a passage 6 is formed coaxially in the chamber 1 in the apparatus or the chamber formed by the housing, with the upper end of this passage 6 opening into the blood outlet 3, and this passage 6 having an end located in the chamber 1 that near the other axial end has at least one opening 7, in which the blood can pass from the chamber 1 into the passage 6. The blood in its flow path thus flows from the upper end 1a of the housing radially on its way from outside toward the inside in the direction of the lower end 1b of the apparatus in order to subsequently flow back through the passage 6 to the blood outlet 3.

On the two axial ends 1a and 1b of the housing, inlet and outlets 8a and 8b are provided for a gas participating in the material exchange, and the gas provided for the material exchange is supplied to the inlet 8a. The cross-sections of the gas inlet 8a and of the gas outlet 8b are each such that the entire chamber cross-section is covered perpendicularly to the axial extension.

The gas flows from the inlet 8a through a multiplicity of gas-permeable fiber tubes that open into the gas inlet 8a and are used for the material exchange, in the direction of the outlet 8b, in which the fiber tubes also open into at the other end in order to reach the gas outlet from there.

For clarity of view, FIG. 1 does not show the multiplicity of the permeable fiber tubes that participate in the material exchange. However, these fiber tubes each extend parallel to the axial direction or the central axis 5 between the inlet 8a and the outlet 8b and each open into this areas, and so the inner volumes of the fiber tubes participating in the material exchange communicate with the gas outlet and the gas inlet.

According to the invention, that in one extension parallel to the central axis 5 or the multiplicity of the fiber tubes participating in the material exchange, additional fibrous or tubular hollow bodies 9 are inserted that also surround the passage 6 in a parallel arrangement. The internal chamber volume, in addition to the blood, is thus filled by both the fiber tubes participating in the material exchange and the fibrous hollow bodies that are particularly not participating in the material exchange and that, according to the invention, have deformable, particularly elastic outer walls and are therefore made, for example, of silicon fiber tubes or hollow silicon tubes or tubes or fibers made of other elastic materials, or of other elastic materials, particularly with a tensile modulus smaller than 0.05 kN/mm$^2$.

In FIG. 1, it can be seen that each of the deformable hollow bodies 9 has an open upper end that opens into the gas inlet 8b, while the lower end at the gas outlet 8b is closed. Each hollow body 9 preferably extends through the entire chamber 1. As a result, the gas that participates in the material exchange fills the interior of the deformable hollow bodies 9 but cannot flow through the hollow bodies.

The deformable hollow bodies 9 together form an overall compressible volume that decreases proportionately as blood pressure increases (for example during the natural systole or a pulsatile blood pump), and expands back to its relaxed original shape as blood pressure decreases (for example during the natural diastole or a pulsatile blood pump). This volume can thus compensate for the blood pressure fluctuations caused by the heartbeat and furthermore, due to the deformability, significantly contribute passively to the pump effect of the heart because blood is displaced from the chamber during relaxation.

The multiplicity of the deformable hollow bodies 9 can thus contribute to generating a windkessel effect that otherwise is achieved by the flexibility of vascular tissue, particularly the pulmonary artery, and significantly relieves pressure on the heart and thus assists pump action.

Particularly in case of a complete substitution of a lung function by such an apparatus according to the invention, the apparatus can thus contribute to a relief of the heart in a passive manner, i.e. without having to actively artificially control the deformable fiber tubes in any way.

Figure 2:
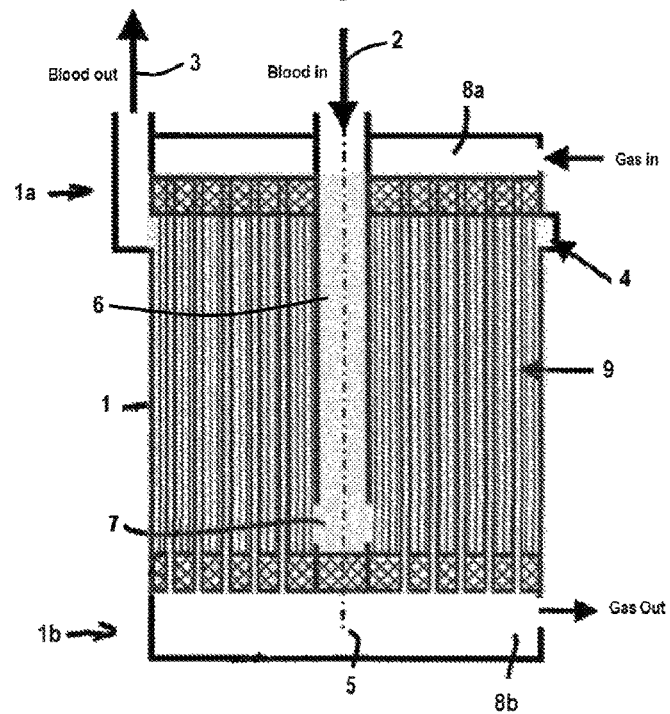
FIG. 2 is a view like FIG. 1 of another apparatus according to the invention.

FIG. 2 shows a variation of FIG. 1, in which the blood inlet 2 and the blood outlet 3 are merely functionally interchanged, and, however, the hollow bodies 9 that provide the windkessel effect, are permanently upwardly closed, particularly also not open or openable at the gas inlet and open at into the gas outlet 8b. The fiber tubes responsible for the gas exchange are again shown as lines between the hollow bodies 9.

Figure 3:
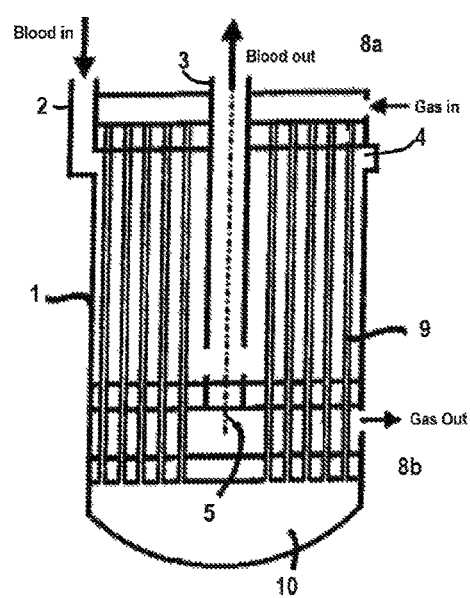
FIG. 3 is another view like FIG. 1 of yet another apparatus according to the invention.

FIG. 3 shows a different possible embodiment, in which the apparatus according to the invention has basically the same design, i.e. the housing encompasses a chamber 1, through which blood flows in the same manner as is realized in FIG. 1 with regard to the flow control. The corresponding design features apply as well.

However, the design is such that the individual deformable hollow bodies 9 that are once again designed so as to be fibrous or tubular and aligned parallel to the material-permeable fiber tubes and parallel to the central axis 5, each with a lower end opening into a common space 10 that is separate both from the chamber and the surroundings, and so the overall available compressible volume is constituted by the sum of the individual volumes of each individual deformable hollow body 9 as well as the volume of the space 10.

Here, it is possible to apply a specifically desired pressure to the space 10 in order to be able to adjust the rigidity or elasticity and compressibility of the overall volume.

The overall arrangement of the overall generated volume and the multiplicity of deformable hollow bodies 9 that are made from a preferably elastic material, thus forms a type of spring element whose the spring constant can be individually changed by the pressure. It is thus possible to application-specifically change the deformation and the volume change of the individual hollow bodies 9 at the existing blood pressure fluctuations caused by the heartbeat.

For example, a connection can also be provided at the separate space 10 for supplying or draining gas in order to change the internal pressure but this is not shown in FIG. 3.

However, instead of arranging only one single space 10 at the lower end of the apparatus, according to the invention two or more separate spaces with a specific number of the overall available hollow bodies 9 can be provided opening into each of these spaces. As a result, the elastic reaction to blood pressure changes can be adjusted differently for different thus-formed groups of hollow bodies 9.

Both embodiments allow, for example, an use inside the body of the apparatus, particularly to completely replace a lung function, or to be operated parallel to the natural lung, where the heart activity can be relieved significantly and particularly in a variably adjustable manner due to the internal deformability of the multiplicity of the hollow bodies 9. Therefore, the heart itself and particularly the right ventricle can be used as pump for operating the apparatus.

Toward the outer surroundings, the space 10 can have at least one flexible wall, for example made of an elastomer (for example, a silicon) or alternatively can be designed so as to be rigid.

As shown in FIGS. 1a and 2, blood inlet and blood outlet can be functionally interchanged, particularly without changing the design.

The invention claimed is:

1. An apparatus for exchanging material between blood and a gas/gas mixture, the apparatus comprising:
    a chamber through which blood can flow and having a gas inlet, a gas outlet, a blood inlet, and a blood outlet;
    a plurality of elongated material-permeable fiber tubes extending along an axis in the chamber and connecting the as inlet to the gas outlet;
    means for flowing the gas/gas mixture through the inlet and then through the fiber tubes and for flowing the blood in through the blood inlet, around the fiber tubes, and then out through the blood outlet;
    at least one internally pressurizable, passive, deformable and hollow element around which the blood can flow in the chamber; and
    means for applying a continuous static pressure to an interior of the passive hollow element such that the deformable hollow element is alternately compressed and expanded by blood-pressure pulsations acting externally on the hollow element of the blood in the chamber for providing a windkessel effect compressing the deformable hollow element from a relaxed shape during a systolic increase in blood pressure and expanding the hollow element during a diastolic decrease of the blood pressure to the relaxed shape.

2. The apparatus according to claim 1, wherein the hollow deformable element operates without any artificial pressure control and is exclusively provided for providing the windkessel effect.

3. The apparatus according to claim 1, wherein the hollow deformable element is a tubular hollow body that is filled with a gas that does not flow through the hollow body and is not open on one of its ends.

4. The apparatus according to claim 3, wherein the chamber holds a multiplicity of the tubular bodies that are impermeable and made of elastic silicon fibers, the fibrous hollow bodies extending parallel to the axis and being surrounded by the fiber tubes while making contact therewith.

5. The apparatus according to claim 3, wherein the deformable hollow body and the material-permeable fiber tubes open into a gas inlet or a gas outlet to which the gas/gas mixture that participates in the material exchange is applied.

6. The apparatus according to claim 1, wherein the deformable hollow body opens into a separate space that can be filled with a gas that does not participate in the material exchange, the space being provided axially downstream in the chamber of the gas outlet.

7. The apparatus according to claim 6, wherein the gas pressure in the separate space is variably statically adjustable.

8. The apparatus according to claim 6, wherein the separate space is provided on one of two axial ends of the apparatus opposite an inlet or outlet for blood.

9. The apparatus according to claim 8, wherein, on one of the two axial ends of the apparatus, a connection for a blood inlet and a blood outlet is provided, one of the connections opening into an annular circumferential compartment that surrounds the chamber, and a passage opens into the other connection and is surrounded by the material-permeable fiber tubes and a plurality of particularly fibrous hollow bodies, and is coaxial to the central axis of the apparatus, and has an opening near the other axial end, through which particularly blood can pass from the chamber into the passage.

10. An apparatus for exchanging material between blood and a gas/gas mixture, the apparatus comprising:
a housing defining a chamber extending along an axis and having axially opposite ends;
means for feeding blood into the chamber at one of the ends and withdrawing the fed-in blood from the chamber at the other of the ends;
a plurality of gas-permeable tubes extending axially in the chamber between the ends;
means for passing the gas/gas mixture through the tubes, whereby material exchange between the blood and the mixture can take place;
a gas-impermeable, passive, flexible, and hollow body in the chamber and compressible by pressure of the blood passing through the chamber; and
means for filling the hollow body with gas at a continuous static pressure.

11. The apparatus defined in claim 10, wherein the gas filling the hollow body is the gas/gas mixture.

12. The apparatus defined in claim 10, wherein there are a plurality of hollow bodies extending axially in the chamber with the tubes.

13. A method of operating an apparatus having
a housing defining a chamber extending along an axis and having axially opposite ends;
means for feeding blood into the chamber at one of the ends and withdrawing the fed-in blood from the chamber at the other of the ends;
a plurality of gas-permeable tubes extending axially in the chamber between the ends; and
means for passing the gas/gas mixture through the tubes, whereby material exchange between the blood and the mixture can take place,
the method comprising the steps of:
providing in the chamber a gas-impermeable, flexible, passive, and hollow body and compressible by pressure of the blood passing through the chamber; and
filling the hollow body with gas at a continuous static pressure and maintaining an internal pressure of the hollow body uniform.

* * * * *